United States Patent [19]

Duerr et al.

[11] 3,960,947

[45] June 1, 1976

[54] CONDENSATION PRODUCTS

[75] Inventors: Dieter Duerr, Bottmingen, Switzerland; Georg Pissiotas, Loerrach, Germany

[73] Assignee: Ciba-Geigy Corporation, Ardsley, N.Y.

[22] Filed: May 14, 1975

[21] Appl. No.: 577,389

Related U.S. Application Data

[62] Division of Ser. No. 218,536, Jan. 17, 1972.

[52] U.S. Cl. .......................... 260/561 R; 260/558 R; 260/558 P; 260/559 B; 260/562 R; 260/562 B
[51] Int. Cl.² ........................................ C07C 103/34
[58] Field of Search ........ 260/561 R, 562 R, 562 B, 260/559 B, 558 R, 558 P

[56] References Cited
UNITED STATES PATENTS

| | | | |
|---|---|---|---|
| 3,520,927 | 7/1970 | Malz et al. .................. | 260/562 R |
| 3,562,326 | 2/1971 | Speziale et al. .............. | 260/562 B |

*Primary Examiner*—C. Davis
*Attorney, Agent, or Firm*—Harry Falber; Frederick H. Rabin

[57] ABSTRACT

Formamidine compounds of the formula

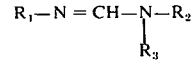

or

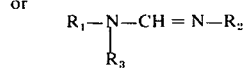

or wherein $R_1$ represents a substituted or unsubstituted phenyl radical, $R_2$ represents hydroogen, alkyl, alkenyl or alkinyl and $R_3$ represents acyl their manufacture and their use in pest control.

4 Claims, No Drawings

CONDENSATION PRODUCTS

This is a division of application Ser. No. 218,536 filed on Jan. 17, 1972.

The present invention relates to formamidines, their manufacture and their use in pest control.

These compounds have the formula

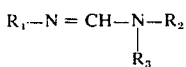

or

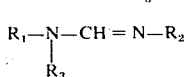

(1)

wherein $R_1$ represents a substituted or unsubstituted phenyl radical, $R_2$ represents hydrogen, alkyl, alkenyl or alkinyl and $R_3$ represents acyl. The number of carbon atoms contained in the alkyl, alkenyl and alkinyl groups which are suitable for $R_2$ is 1 to 18, or 2 to 18, but is preferably 1 to 4 or 3 to 4. These groups may be branched or straight-chain, interrupted in the chain by hetero atoms, for example oxygen, sulphur, or nitrogen, unsubstituted or substituted. Examples of such radicals include: methyl, ethyl, propyl, isopropyl, n-, i-, sec.- and tert. butyl, 2-chloroethyl, cyanomethyl, allyl, methallyl, 3-chloroalkyl, propargyl, isobutinyl.

The acyl radical represented by $R_3$ may be substituted or unsubstituted, saturated or unsaturated, and is derived primarily from aliphatic or aromatic carboxylic acids, or free carbonic acid or derivatives thereof.

On account of their activity, preferred compounds are those of the formula

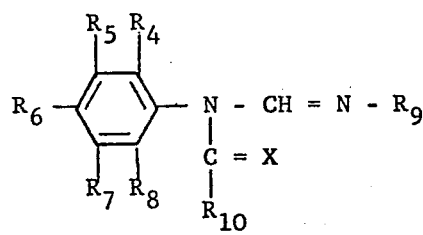

(II)

or

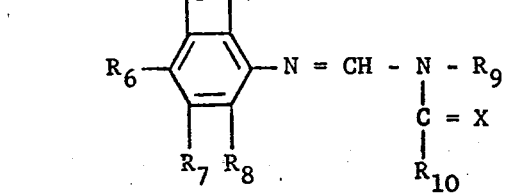

wherein $R_4$ to $R_8$ each represent hydrogen, fluorine, chlorine, bromine, iodine, alkyl or alkoxy containing from 1 to 4 carbon atoms, alkenyloxy or alkinyloxy containing from 3 to 4 carbon atoms, $-SO_2NH_2$, $-SO_2N(C_1-C_4\ alkyl)_2$, $-SO_2(C_1-C_4)alkyl$, $-CF_3$, $-NO_2$ or $-CN$, $R_9$ represents hydrogen, alkyl containing from 1 to 4 carbon atoms, alkenyl or alkinyl containing from 1 to 4 carbon atoms, $R_{10}$ represents hydrogen, alkyl containing from 1 to 18 carbon atoms, alkenyl containing from 2 to 4 carbon atoms, substituted or unsubstituted phenyl or naphthyl or the groups $-NH(C_1-C_{18}-alkyl)$, $-N(C_1-C_4\ alkyl)_2$,

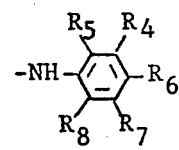

or $-O(C_1-C_4\ alkyl)$ and X represents oxygen or sulphur.

Preferred compounds of the formula II have the formulae

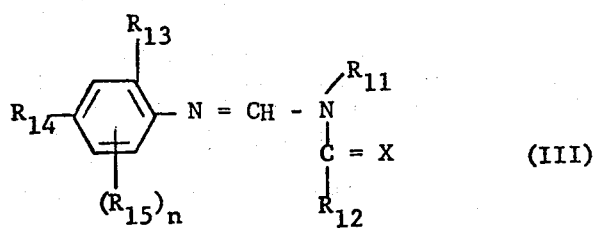

(III)

or

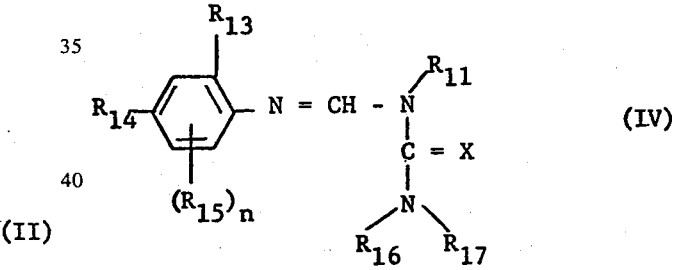

(IV)

or

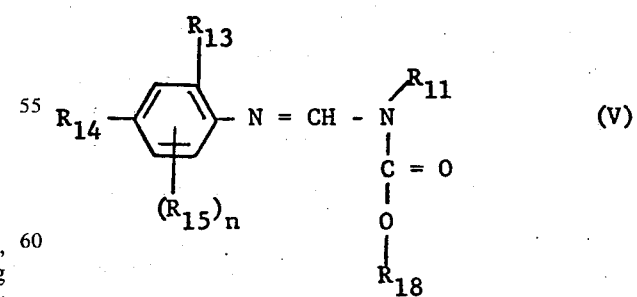

(V)

wherein $R_{11}$ represents alkyl containing from 1 to 4 carbon atoms or alkenyl containing from 3 to 4 carbon atoms, $R_{12}$ represents hydrogen, alkyl containing from 1 to 12 carbon atoms, alkenyl containing from 3 to 4 carbon atoms, phenyl or naphthyl, $R_{13}$ represents hydrogen, alkyl containing from 1 to 4 carbon atoms, $-CF_3$ or halogen, $R_{14}$ represents hydrogen, alkyl or alkoxy each containing from 1 to 4 carbon atoms, alkenyloxy or alkinyloxy each containing from 3 to 4 carbon atoms or halogen, $R_{15}$ represents hydrogen, halogen, alkyl containing from 1 to 4 carbon atoms, $-NO_2$ or $-CF_3$, $R_{16}$ represents hydrogen or alkyl containing from 1 to 4 carbon atoms, $R_{17}$ represents hydrogen, alkyl containing from 1 to 14 carbon atoms or substituted or unsubstituted phenyl, $R_{18}$ represents alkyl containing from 1 to 4 carbon atoms, phenyl, or 2-methyl-4-chlorophenyl, X represents oxygen or sulphur, and $n$ represents the numbers 1, 2, or 3.

The substituents at the alkyl, alkenyl, alkinyl, acyl, naphthyl and phenyl radicals may be of the first or second order.

By substituents of the first order are meant electron donors which increase the basicity. These include the the following groups: halogen atoms, for example fluorine, chlorine, bromine, or iodine, alkoxy and alkylthio groups containing from 1 to 4 carbon atoms and which may be branched or unbranched, but are preferably unbranched and contain from 1 to 2 carbon atoms; lower alkoxyalkyl and alkyl groups, to which the definitions given hereinabove also apply here; secondary and tertiary amino groups, preferred substitutents being lower alkyl and alkanoyl groups; hydroxyl and mercapto groups. The naphthyl and phenyl radical may also be substituted by alkyl, mono- and dihalogenoalkyl groups.

By substituents of the second order are meant acidifying electron donors. These include the following groups: nitro and cyano groups; trihalogenoalkyl groups, in which halogen represents preferably fluorine or chlorine; lower alkylsulphonyl groups which contain a branched or unbranched alkyl radical having 1 to 4 carbon atoms, preferably one unbranched alkyl radical having 1 to 2 carbon atoms; sulphamyl and sulphamido groups, it being possible for the amino groups to carry one or two substituents, preferably lower alkyl groups, as defined hereinabove.

The compounds of the formula (I) can be manufactured according to methods which are in themselves known, for example by acylating formamidines of the formulae

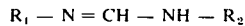

   (VI)

wherein $R_1$ and $R_2$ have the meanings given for the formula I, with anhydrides or halides of aliphatic or aromatic carboxylic acids or of carbonic acid or with derivatives thereof, if necessary using acid binding agents.

The following bases may be cited as examples of suitable acid binding agents: tertiary amines, such as triethylamine, dimethyl aniline, pyridine, pyridine bases; inorganic bases, such as hydroxides and carbonates of alkali and alkaline earth metals, preferably sodium and potassium carbonate.

It is advisable to carry out the reaction in an inert solvent, of which the following may be cited as examples, aromatic hydrocarbons, such as benzene, toluene, gasolines, chlorobenzene, polychlorobenzenes, bromobenzene; chlorinated alkanes containing 1 to 3 carbon atoms; ethers, such as dioxan, tetrahydrofuran; esters, such as ethyl acetate; ketones, such as methyl ethyl ketone, diethyl ketone.

The starting materials of the formula VI are in part known compounds. These compounds can be manufactured according to methods which are in themselves known, for example by heating the corresponding arylisocyanates with an amide of formic acid.

The compounds of the formula I have a broad biocidal activity spectrum and may be used to combat vegetable and animal pests, for example as bactericides, viricides, selective herbicides, molluscicides and anthelminthics, and also as abscission agents, defoliants and plant growth inhibitors.

The compounds of the formula I also have a selective action against weeds in cultures of crop plants. This action can be attained in the preemergent and postemergent processes and is particularly observed in important large-scale crops, for example grain, rice, maize, sugar beet, soya, cotton, lucerne, potatoes and others. The rates of application herein may vary within wide limits, for example between 0.1 to 10 kg of active substance per hectare; but preferably 0.5 to 5 kg per hectare are employed. A total herbicidal and also defoliating action is observed with the use of higher rates of application. Such action is always advantageous whenever the soil is to be prepared for a new planting while remains of a previous crop are still present.

In particular, the compounds of the formula I possess insecticidal and acaricidal properties and may be used against all development stages such, for example, as eggs, larvae, pupae, nymphs and adults of insects and representatives of the order acarina, for example against insects of the families:

| | |
|---|---|
| Teltigonidae | Tenebrionidae |
| Gryllidae | Chrysomelidae |
| Gryllotalpidae | Bruchidae |
| Blattidae | Tineidae |
| Peduviidae | Noctindae |
| Phyrrhocoriae | Lymatriidae |
| Cimicidae | Pyralidae |
| Delphacidae | Culicidae |
| Aphididae | Tipulidae |
| Diaspididae | Stomoxydae |
| Pseudococcidae | Trypetidae |
| Scarabaeidae | Muscidae |
| Dermestidae | Calliphoridae and |
| Coccinellidae | Pulicidae |

Acarida of the families:
Ixodidae
Argasidae
Tetranychidae and
Dermanyssidae.

The insecticidal or acaricidal action can be substabtially broadened and adapted to the particular circumstances by the addition of other insecticides and/or acaricides.

Suitable additives include, for example, the following active substances:

Organic derivatives of phosphorus

Bis- O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)

Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethylS,S-dipropyldithiophosphate -ethyl-S,S-dipropyldithiophosphate
O,O-dimethyl-S-(N-methyl-N-formylcabamoylmethyl)-dithiophosphate (FORMOTHION)
O,O-dimethyl-S-(N-methylcabamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4-5-trichlorophenylthiophosphate (RONNEL)
O-ethyl-0,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert. butyl-2-chlorophenyl-N-methyl-O-methylamidophosphate (CRUFOMATE)
O,O-dimethyl-O-(3-methyl-4-methylmercaptophenyl)thiophosphate (FENTHION)
Isopropylamino-O-ethyl-O-(4-methylmercapto-3-methylphenyl)phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)-phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-O-(3-chloro-4-methyl-2-oxo-2-H-1-benzopyran -7-yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol -5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)thiophosphate (DIAZINON)
O,O-diethyl-O-(2-chinoxalyl)thiophosphate
O,O-dimethyl-S-(4-oxo-1,2,3-benzotriazin-3(4H)-ylmethyl)-dithiophosphate (AZINPHOSMETHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O( or S)-2-(ethylthioethyl)thiophosphate (DEMETONS-METHYL)
2-(O,O-dimethyl-phosphoryl-thiomethyl)-5-methoxypyron-4-3,4-dichlorobenzyl-triphenylphosphoniumchloride
O,O-dimethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-diemthyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
0,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate O-[p-(-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphate (BUTONATE)
O,O-dimethyl-O-(2,2-dichloro-1-methoxy-vinyl)phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethyl-phenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene (1,5)
O-methyl-O-(2-i-propoxycarbonyl-1-ethylamidothiophosphate.

Carbamic acid derivatives 1-naphthyl-N-methylcarbamate (CARBARYL)
2-butinyl-4-chlorophenylcarbamate
4-dimethylamino-3-tolyl-N-methylcarbamate (AMINOCARB)
4-methylthio-3,5-xylyl-N-methylcarbamate (METHIOCARB)
2-chlorophenyl-N-methylcarbamate (CPMC)
1-(dimethylcarbamoyl)-5-methyl-3-pyrazolyl-N,N-dimethylcarbamate (DIMETHILAN)
2,3-dihydro-2,2-dimethyl-7-benzofuranyl-N-methylcarbamate (CARBOFURAN)
2-methyl-2-methylthiopropional-O-(methylcarbamoyl)-oxime (ALDICARB)
8-quinaldyl-N-methylcarbamate and salts thereof
3-isopropyl-5-methylphenyl-N-methylcarbamate (PROMECARB)
2-(1,3-dioxolan-2-yl)-phenyl-N-methylcarbamate (DIOXACARB)
2-(4,5-dimethyl-1,3-dioxalan-2-yl)-phenyl-N:methyl-carbamate
2-(1,3-dithiolan-2-yl)-phenyl-N-methylcarbamate
2-(1,3-dithiolan-2-yl)-phenyl-N,N-dimethylcarbamate
2-isopropoxyphenyl-N-methylcarbamate (APROCARB)
4-diallylamino-3,5-xylyl-N-methylcarbamate (ALLYXICARB)
1-isopropyl-3-methylpyrazol-5-yl-N,N-dimethylcarbamate (ISOLAN)
1-methylthioethylimino-N-methylcarbamate (METHOMYL)
2-[propargylethylamino]-phenyl-N-methylcarbamate
2-[propargylmethylamino]-phenyl-N-methylcarbamate
2-[dipropargylamino]-phenyl-N-methylcarbamate
3-methyl-4-[dipropargylamino]-phenyl-N-methylcarbamate
3,5-dimethyl-4-[dipropargylamino]-phenyl-N-methylcarbamate
2-[allylisopropylamino]-phenyl-N-methylcarbamate

Nitrophenols and derivatives 4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethrin I
pyrethrin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-quinoxaline (Quinomethionate]
(I)-3-(2-furfuryl)-2-methyl-4-oxocyclopent-2-enyl(I)-(cis+trans)-chrysanthemum-monocaboxylate [Furethrin]
2-pivaloyl-indane-1,3-dione [Pindon]
N'-(4-chloro-2-methylphenyl)-N,N-dimethylformamidine [Chlorophenamidin)
4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzensulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

The active substances of the formula I also possess excellent fungicidal properties against phytopathogenic fungi in cultivated plants of the most diverse kinds, such as cereals, maize, rice, vegetables, ornamental plants, fruit varieties, grapevines, farm product etc.

Using the active substances of the invention it is possible to check or destroy fungus infections which have occured on fruit, blossoms, leaves, stems, tubers and roots, and parts of plants which then grow later also remain free from such infections. The active substances of the formula I are active against the phytopathogenic fungi belonging to the following classes, orders and species of fungi: Oomycetes such as Plasmodiophora types, Aphanomyces types, Pythium types, Phytophthora types, e.g. (*Phytophthora infestans, Phytophthora cactorum*), Plasmopara types, e.g. (*Plasmopara viticola*), Bremia types (*Bremia lactucae*), Peronospora types, e.g. (*Peronospora tabacina*), Pseudoperonospora types, e.g. (*Pseudoperonospora humuli*). Zygomycetes such as Rhizopus types. Ascomycetes such as Eurotiales, such as Aspergillus types, Penicillium types, e.g. (*Penicillium digitatum,* Penicillium italicum), Taphrinales, such as Taphrina types, e.g. (Taphrina deformans), Erysiphales, such as Erysiphes types, e.g. (*Erysiphes cichoracearum, Erysiphes graminis*), Podosphaera leucotricha, Sphaerotheca types (*Sphaerotheca pannosa*), Uncinula types (*Uncinula necator*), Helotiales, such as Monilina types (Monilinia [Sclerotinia] fructicola, Monilinia laxa), Diplocarpon types (*Diplocarpon rosae*), Pseudopeziza types, Sphaeriales, such as Nectria types (*Nectria galligena*), Ceratocystis types, Pseudosphaeriales, such as Venturia types (*Venturia inaequalis*), Mycosphaerella types, Ophiobolus types (*Ophiobolus graminis*), Cochliobolus types (Helminthosphorium) miyabeanus), Cercospora types, (*Cercospora beticola, Cercospora musae*). Basidiomycetes, such as Aphyllophorales, Pellicularia types, e.g. (Pellicularia filamentora = (*Rhizoctonia solani*) ), Uredinales, such as Puccinia types, e.g. (*Puccinia triticina*), Uromyces types (*Uromyces phaseoli*), Hemileia types, (*Hemileia vastatrix*), Cronatrium types (*Cronartium ribicola*), Phragmidium types (*Phragmidium subcorticium*), Gymnosporangium types.

Denteromycetes = (*Fungi imperfecti*) such as Piricularia types, e.g. (*Piricularia oryzae*), Corynespora types. Thielaviopsis types, Clasterosporium types, Botrytis types (*Botrytis cinerea*), Cladosporium types, Alternaria types, (Alternaria solani), Verticillium types (*Verticillium albo-atrum*), Phielaphora types, Melanconiales, such as Colletotrichum types, Fusarium types such as (*Fusarium oxysporum, Fusarium nivale*), Gloesporium types (*Gloesporium fructigenum*), Sphaeropsidales, e.g. Septoria types (*Septoria apicola*), Diplodia types, (*Diplodia natalensis*), Mycelia sterilica, e.g. Sclerotium types (*Sclerotium rolfsii*).

The active substances according to the invention can also be used for treating seed grain, fruit, tubers etc. and for protecting them from fungus infections, for example from smut fungi of all kinds, such as:
Ustilaginales, such as Ustilago types (*Ustilago avenae*)
Tilletia types (*Tilletia tritici*),
Urocystis and Tuburcinia types
Phoma types (*Phoma betae*).

To broaden their activity spectrum the active substances of the formula I may contain in admixture bactericides, fungistatic agents, bacteriostatic agents, nematocides, and/or, for example, the following fungicides:
dodecylquanidine acetate (DODINE)
pentachloronitrobenzene (QUINTOZENE)
pentachlorophenol (PCP) 2-(1methyl-n-propyl)-4,6-dinitrophenyl-2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenyl-sulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)

zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxypyrimidine
methyl-N-bebzimidazole-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine pentachlorobenzyl alcohol.

Due to their biocidal properties the compounds of the formula I are suitable for the disinfection and protection of various materials before attack by bacteria and fungi. In this connection it is particularly advantageous that the compounds of the formula I have no poisonous side effects when used in the concentrations necessary for the disinfection and protection of the materials.

Furthermore, the new compounds of the formula I possess good nematocidal properties and may be used to combat, for example, the following plant parasitic nematodes:

Meloidogyne spp.
Heterodera spp.
Ditylenchus spp.
Pratylenchus spp.
Helicotylenchus spp.
Tylenchorhynchus spp.
Rotylenchus spp.
Rotylenchulus spp.
Tylenchulus spp.
Belonolaimus spp.
Trichodorus spp.
Radopholus spp.
Longidorus spp.
Xiphinema spp.

The compounds of the formula I may be used as pure active substance or together with suitable carriers and/or additives. Suitable carriers and additives can be solid or liquid and correspond to the substances conventionally used in formulation technique such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application terminology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms

Dusts, tracking agents, granules, coated, granules, impregnated granules and homogeneous granules.

Liquid forms:
a. active substances which are dispersible in water: wettable powders, pastes, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SIO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the folowing: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentuoned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives mentioned above that, in wettable powder, the solid particle size of from 0.02 to 0.04 and in pasts, of 0.03 is not exceeded. To produce emulsifiable concentrates and pastes, dispersing agents such as those cited above, organic solvents and water are used. Examples of suitable solvents are the following: alcohols, benzene, xylenes, toluene, dimethyl sulfoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0:1% to 95%, in which connection it should be mentioned that in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

a.
5 parts of active substance
95 parts of talcum
b.
2 parts of active substance
1 part of highly disperse silica
97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25 %, and (d) a 10% wettable powder:

a.
40 parts of active substance,
5 parts of sodium lignin sulphonate,
1 part of sodium dibutyl-naphthalene sulphonate,
54 parts of silica acid.
b.
25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silica acid,
19.5 parts of Champagne chalk,
28.1 parts of kaolin.
c.
25 parts of active substance,
2.5 parts of isooctylphenoxy-polyoxyethylene-ethanol,
1,7 parts of Champagne chalk/hydroxyethyl cellulose mixture (1:1),
8.3 parts of sodium aluminium silicate,
16.5 parts of kieselguhr,
46 parts of kaolin.
d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b.
25 parts of active substance,
2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to ptoduce, by dilution with water, emulsion of any desired concentration.

Spray

The following constituents are used to prepare a 5% spray:
5 parts of active substance,
1 part of epichlorohydrin,
94 parts of benzine (boiling limits 160° – 190°C).

EXAMPLE 1

36.5 Grams of N-4-chloro-2-methyl-phenyl-N'-methylformamidine are treated in a distilling apparatus with 26.5 g of propionic anhydride. Distillation of the reaction product yields N-4-chloro-2-methyl-phenyl-N'-propionyl-N'-methylformamidine, melting point 132°C/0.001 mm Hg.

EXAMPLE 2

36.5 Grams of N-4-chloro-2-methyl-phenyl-N'-methylformamidine are dissolved in 100 ml of benzene and the solution is treated with 24 g of phenylisocyanate. The product is precipitated in the form of crystals by addition of 250 ml of hexane, yielding N-4-chloro-2-methyl-phenyl-N'-methyl-N'-phenylcarbamoyl-formamidine; melting point 98°–100°C.

EXAMPLE 3

36.5 Grams of N-4-chloro-2-methyl-phenyl-N'-methylformamidine are dissolved in 400 ml of benzene and the solution is treated with 30 g of 3-methylphenylisothiocyanate. Upon completion of the reaction, the reaction mixture is evaporated and the crude product recrystallised from benzene/petroleum ether, yielding N-(4-chloro-2-methyl-phenyl)-N'-methyl-N'-(3-methylphenylthiocarbamoyl)-formamidine; melting point 94°–95°C.

EXAMPLE 4

54.8 Grams of N-4chloro-2-methyl-phenyl-N'-methylformamidine are dissolved in 400 ml of benzene and the solution is treated with 13.5 ml of ethyl chloroformate. Upon completion of the reaction, the hydrochloride salt of the formamidine simultaneously used as base is filtered off and the filtrate evaporated, to yield N-4-chloro-2-methylphenyl-N'-methyl-N'-carboethoxyformamidine.

By proceeding analogously to Examples 1 to 4 the following compounds are also manufactured:

| Structure | Boiling Point | Melting Point |
|---|---|---|
| Cl-(CH$_3$)C$_6$H$_3$-N=CH-N(COCH$_3$)(CH$_3$) | 124°C/0,01 mmHg | 70°C |
| Cl-(Cl)C$_6$H$_3$-N=CH-N(CONH-CH$_3$)(CH$_3$) | | 112–113°C |
| Cl-(CH$_3$)C$_6$H$_3$-N=CH-N(COCH$_3$)(C$_2$H$_5$) | 118–112°C/0,07mmHg | |
| Cl-(CH$_3$)C$_6$H$_3$-N=CH-N(COCH$_3$)(C$_3$H$_7$(n)) | 116°C/0,02mmHg | |
| Cl-(CH$_3$)C$_6$H$_3$-N=CH-N(COCH$_3$)(C$_3$H$_7$(i)) | 110°C/0,03 mmHg | |
| Cl-(CH$_3$)C$_6$H$_3$-N=CH-N(CHO)(C$_3$H$_7$(i)) | 124–126°C/0,04 mmHg | |
| Cl-(CH$_3$)C$_6$H$_3$-N=CH-N(CO-CH$_3$)(C$_4$H$_9$(n)) | 138–141°C/0,2 mmHg | |

| | -continued | |
|---|---|---|
| | Boiling Point | Melting Point |
| 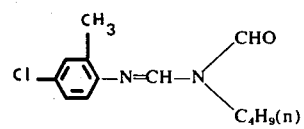 | 130°C/0,08 mmHg | |
| 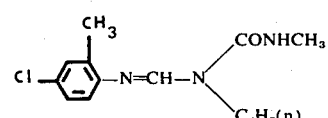 | | Harz |
| 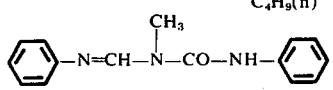 | | 130–132°C |
| 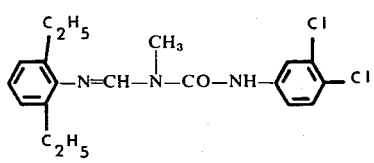 | | 108–110°C |
| 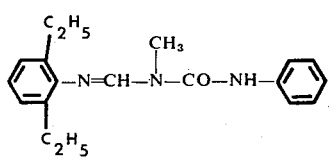 | | 143–144°C |
| 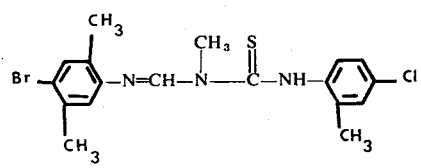 | | 96–97°C |
| 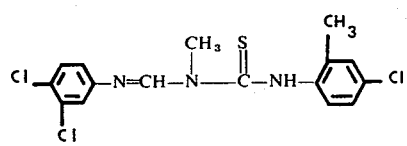 | | 88–89°C |
| 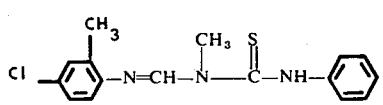 | | 106–107°C |
| 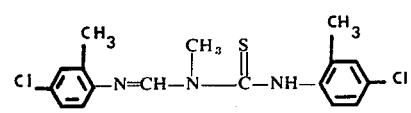 | | 91–92°C |
| 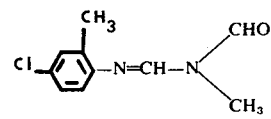 | 125°C/0,06 mm Hg | |

-continued
| | Boiling Point | Melting Point |
|---|---|---|
| 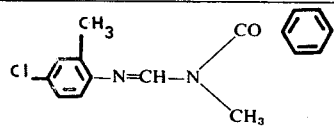 | 144°C/0,05 mm Hg | |
| 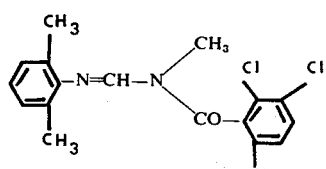 | 145°C/0,15 mm Hg | |
| 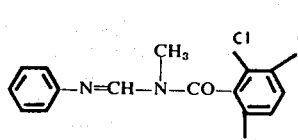 | | 116–118°C |
| 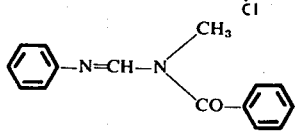 | 145°C/0,15 mm Hg | |
| 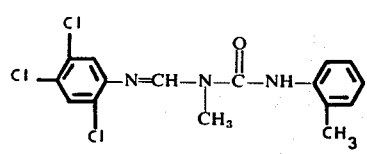 | | 178–179°C |
| 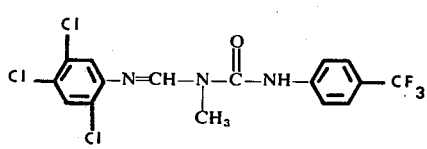 | | 162–163°C |
| 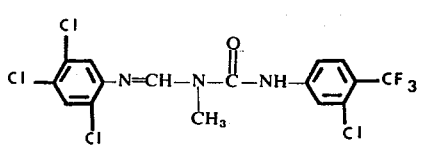 | | 179–180°C |
| | Melting Point |
|---|---|
| 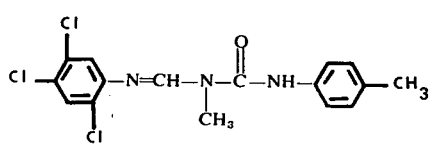 | 191–192°C |

-continued
Melting Point
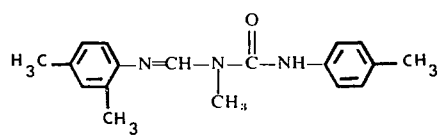 90–91°C
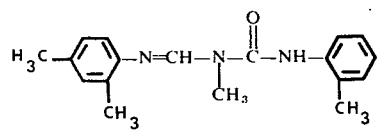 90–91°C
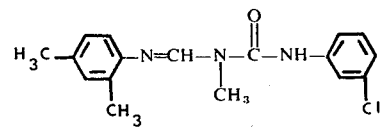 105–106°C
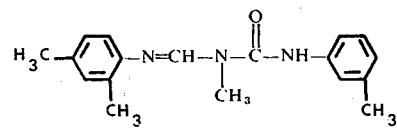 81–82°C
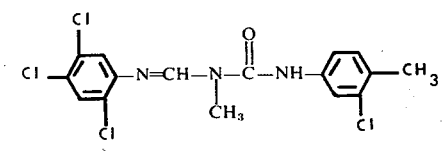 191–192°C
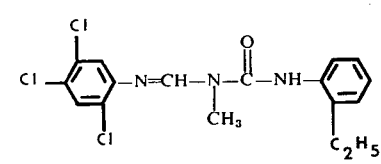 139–140°C
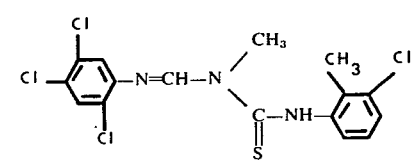 99–100°C
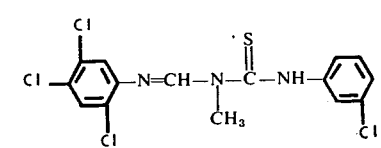 120–121°C
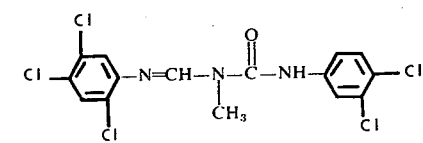 166–167°C -continued

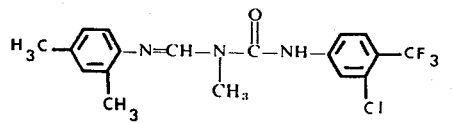 100–101°C

| R (Br, CH₃ substituted aryl N=CH-N(CH₃)-R) | Melting Point |
|---|---|
| H₃C–C₆H₄–NH–C(=O)– | 111–112°C |
| 2,6-(C₂H₅)₂–C₆H₃–NH–C(=O)– | 190–191°C |
| 2-C₂H₅–C₆H₄–NH–C(=O)– | 102–103°C |
| 2-CH₃–C₆H₄–NH–C(=O)– | 118–119°C |

| R (Cl, CH₃ substituted aryl N=CH-N(CH₃)-R) | Melting Point |
|---|---|
| 2-CH₃–C₆H₄–NH–C(=O)– | 103–104°C |
| 3-CH₃–C₆H₄–NH–C(=O)– | 96–97°C |

| R (continued — Cl, CH₃ substituted aryl N=CH-N(CH₃)-R) | Melting Point |
|---|---|
| H₃C–C₆H₄–NH–C(=O)– | 109–111°C |
| 2-C₂H₅–C₆H₄–NH–C(=O)– | 76–77°C |
| 2,6-(C₂H₅)₂–C₆H₃–NH–C(=O)– | 180–181°C |
| 4-n-C₄H₉O–C₆H₄–NH–C(=O)– | 127–128°C |
| CF₃–C₆H₄–NH–C(=O)– | 98–100°C |
| 2-Cl–C₆H₄–NH–C(=O)– | 120–121°C |
| 4-Cl–C₆H₄–NH–C(=O)– | 128–129°C |
| 2,3-Cl₂–C₆H₃–NH–C(=O)– | 79–80°C |

25
-continued

Structure: Cl-C6H3(CH3)-N=CH-N(CH3)-R

| R | Melting Point |
|---|---|
| 3,4-dichlorophenyl-NH-C(O)- | 139–140°C |
| 4-chloro-2-methylphenyl-NH-C(O)- | 130–131°C |
| 3-chloro-5-methylphenyl-NH-C(O)- | 116–117°C |
| 3-chloro-5-ethylphenyl-NH-C(O)- | 79–80°C |
| 3-chloro-5-trifluoromethylphenyl-NH-C(O)- | 155–156°C |
| 3-chloro-5-trifluoromethylphenyl-NH-C(O)- | 115–116°C |
| 3-methyl-5-nitrophenyl-NH-C(O)- | 185–186°C |
| (n)C4H9-C6H4-NH-C(O)- | $n_{25}$: 1,5870 |
| CH3O-C6H4-NH-C(O)- | 91–92°C |
| C2H5-NH-C(O)- | 74–75°C |
| (CH3)2CH-NH-C(O)- | 56–57°C |
| C4H9(n)-CH(C2H5)-CH2-NH-C(O)- | oil |

26
-continued

Structure: Cl-C6H3(CH3)-N=CH-N(CH3)-R

| R | Melting Point |
|---|---|
| CH2=CH-CH2-NH-C(O)- | 68–69°C |
| 2-chlorophenyl-NH-C(S)- | 81–82°C |
| 3-chlorophenyl-NH-C(S)- | 99–100°C |
| 2-methoxy-5-methylphenyl-NH-C(O)- | 147–149°C |
| CH3-O-C(O)- | $n_{25}$: 1,5662 |
| CH2=CH-C(O)- (H3C) | $n_{25}$: 1,5856 |
| (H3C)2CH-O-C(O)- | $n_{25}$: 1,5423 |
| CH3-(CH2)3-O-C(O)- | $n_{25}$: 1,5296 |
| (n)H9C4-NH-C(O)- | $n_{25}$: 1,5627 |
| C6H5-O-C(O)- | $n_{25}$: 1,5948 |
| (H3C)2CH-C(O)- | $n_{25}$: 1,5655 |
| 2-ethoxyphenyl-NH-C(O)- | 127–128°C |
| 3-methylphenyl-C(O)- | 106–108°C |
| 2-chloro-6-methylphenyl-NH-C(S)- | 105°C |

-continued
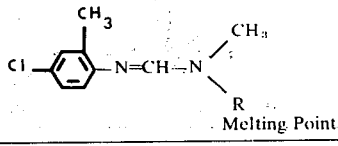
| R | Melting Point |
|---|---|
| 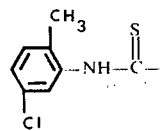 | 103–104°C |
| 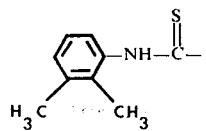 | 109–110°C |
| 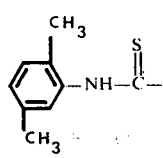 | 97°C |
| 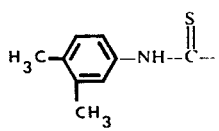 | 93–94°C |
| 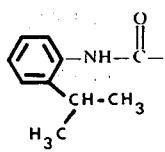 | 120–121°C |
-continued
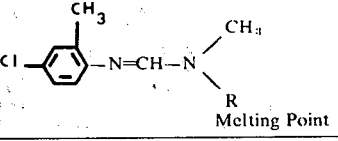
| R | Melting Point |
|---|---|
| 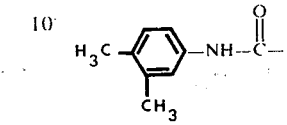 | 134–135°C |
| 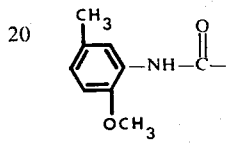 | 149–150°C |
| 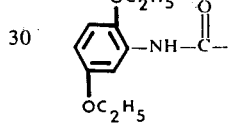 | 105–106°C |
| 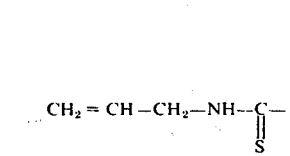 | 90–91°C |
| | Melting Point |
|---|---|
| 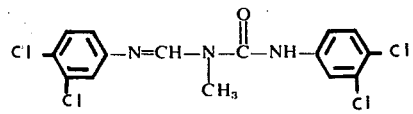 | 123–124°C |
| 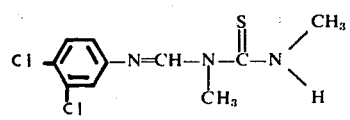 | 116–119°C |
| 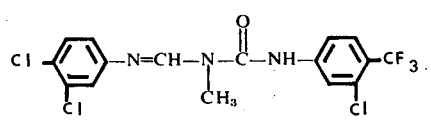 | 145–146°C |
| 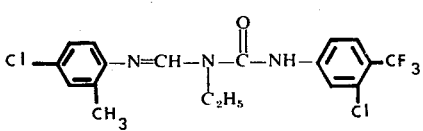 | 102–105°C |

-continued

| | Melting Point |
|---|---|
| 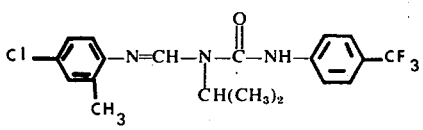 | 99–100°C |
| 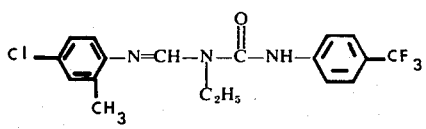 | 108–109°C |
| 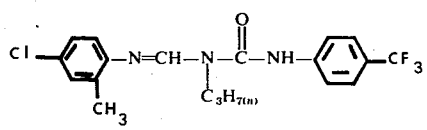 | 118–120°C |
| 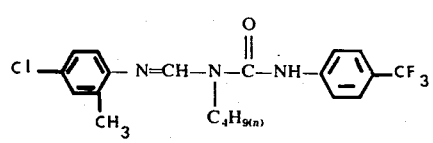 | 74–75°C |

EXAMPLE 5

Insecticidal Ingest poison action

Cotton and potato plants are spryed with a 0.05 % aqueous emulsion (obtained from a 10 % emulsifiable concentrate).

After the coating has dried, Disdercus fasciatus nymphs are settled on the cotton plants and Colorado potato beetle larves (*Leptinotarsa decemlineata*) on the potato plants. The test is carried out at 24°C and 60 % relative humidity.

The compounds according to Examples 1 to 4 have an ingest poison action against *Disdercus fasciatus* and *Leptinotarsa decemlineata*.

EXAMPLE 6

Systemic insecticidal action

To determine the systemic action, rooted bean plants (Vicia fabae) are put into a 0.01% aqueous active substance solution (obtained from a 10% emulsifiable concentrate). After 24 hours, aphids (*Aphis fabae*) are placed on the parts of the plant above the soil. The aphids are protected from contact and gas action by means of a special device. The test is carried out at 24°C and 70% relative humidity. In the above test the compounds according to Examples 1 to 4 have a good systemic action against *Aphis fabae*.

EXAMPLE 7

Acaricidal Action a. Action on mites (*Teranychus urticae*)

To test the acaricidal action, bean leaves attacked by adults, latent stages and eggs of the red spider mite (*Tetranychus urticae*) were treated with an 0.05 % aqueous emulsion of the substance to be tested (prepared from a 25 % emulsifiable concentrate). The test was evaluated after 6 days. Strains of the red spider mite which are resistant to phosphoric esters were used as test subjects.

b. Action on ticks (*Boophilus microplus*) and their development stages

For the following test, 10 adult ovipositing ticks were immersed for 3 minutes in aqueous active substance emulsions (concentrations see column 2).

The ticks were then kept at 27°C and 80 % relative humidity. Oviposition was determined on the 5th, 10th, and 15th day.

The compounds tested according to the above tests (a) and (b) according to Example 1 to 4 displyed good action against Tetranychus urticae and Boophilus microplus.

EXAMPLE 8

Fungicidal action a. Action against Botrytis cinerea on *Vicia faba*

Fully developed, uniformly large leaves of *Vicia faba*, which have been sprayed dripping wet from a spraying device with a broth (0.05% content of active substance) prepared from an active substance formulated as a 10% wettable powder, were placed three at a time in Petri dishes lined with filter paper. When the leaves were dry again, they were infected with a freshly prepared, standardised spore suspension of the fungus (concentration: 100'000 spores/ml) and kept for 48 hours in a humid atmosphere at 20°C. After this time, the leaves displayed black, initially dot-shaped specks which rapidly spread. The number and size of the infected areas served as a yardstick for determining the effectiveness of the test substance.

b. Action against Erysiphe cichoracearum on *Cucumis sativus*

Young *Cucumis sativus* plants were sprayed with a spore suspension after they had been sprayed with a 0.05% suspension of the active substance formulated as wettable powder and after the spray coating had dried. The degree of attack (extent of the leaf surface coated with the mycel coating) on the infected, treated leaves was assessed after 8 days in a greenhouse at approx. 23°C in comparison with untreated, infected controls.

c. Action against *Uromyces appendiculates* on *Phaseolus vulgaris* Phaseolus vulgaris plants in the 2-leaf stage were sprayed until dripping wet with a suspension of the active substance formulated as wettable powder (concentration = 0.05% of active substance). After the spray coating had dried, the plants were infected with a fresh spore suspension of bean rust and then kept for 1 day in a humid chamber, then for 12 days in a greenhouse at 20°–22°C.

The number and size of the rust pustules served as a yardstick for assessing the effectiveness of th active substances.

d. Action against *Phytophthora infestans* on *Solanum Lycopersicum*

S. Lycopersicum plants of the same variety and in the same development stage were treated with a broth of 0.05% active substance (prepared from the active substance formulated as a wettable powder). After the coating layer had dried, the dry plants were sprayed dripping wet with a zoospore suspension of Ph. Infestans. They were then kept for 6 days in a greenhouse at 18°–20°C and high humidity (95–100%), after which time they displayed typical leaf specks. The evaluaton of the tested substance was based on their number and size.

The compounds according to Examples 1 to 4 displayed good fungicidal action in the above tests (a) to (d).

EXAMPLE 9

Action against soil nematodes

To test the action against soil nematodes, the active substance (in the concentration indicated in each case is applied to and intimately mixed with soil infected with root gall nematodes (*Meloidgyne Avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Examples 1 to 4 display good action against *Meloidgyne avenaria*.

We claim:

1. A compound of the formula

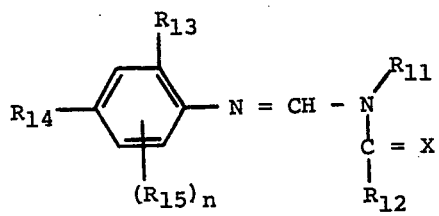

or (III)

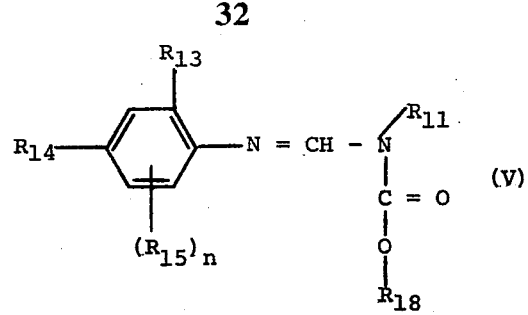

wherein $R_{11}$ represents alkyl containing from 1 to 4 carbon atoms or alkenyl containing from 3 to 4 carbon atoms, $R_{12}$ represents hydrogen, alkyl containing from 1 to 12 carbon atoms, alkenyl containing from 3 to 4 carbon atoms, phenyl or naphthyl, $R_{13}$ represents hydrogen, alkyl containing from 1 to 4 carbon atoms, $-CF_3$ or halogen, $R_{14}$ represents hydrogen, alkyl or alkoxy each containing from 1 to 4 carbon atoms, alkenyloxy or alkinyloxy each containing from 3 to 4 carbon atoms or halogen, $R_{15}$ represents hydrogen, halogen, alkyl containing from 1 to 4 carbon atoms, $-NO_2$ or $-CF_3$, $R_{18}$ represents alkyl containing from 1 to 4 carbon atoms, phenyl or 2-methyl-4-chlorophenyl, X represents oxygen or sulphur, and n represents the numbers 1, 2, or 3.

2. The compound according to claim 1 of the formula

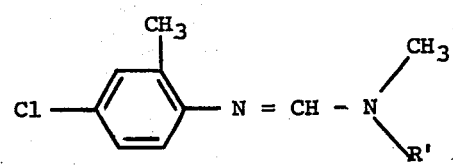

wherein R' represents

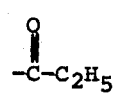

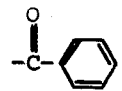

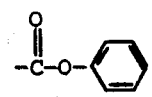

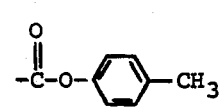

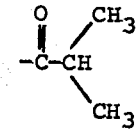

3. A compound according to claim 1 of the formula
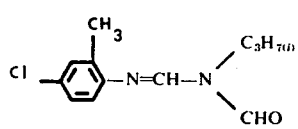
4. A compound according to claim 1 of the formula
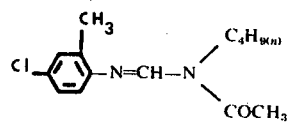
* * * * *